(12) United States Patent
Moran

(10) Patent No.: US 7,093,770 B1
(45) Date of Patent: Aug. 22, 2006

(54) DEVICE FOR DISPENSING ANIMAL SCENT ATTRACTANT FOR BEHIND ANKLE OF USER

(76) Inventor: Tony Kenneth Moran, 25489 Tanksley Rd., Bokoshe, OK (US) 74930-2337

( * ) Notice: Subject to any disclaimer, the term of this patent is extended or adjusted under 35 U.S.C. 154(b) by 0 days.

(21) Appl. No.: 11/293,539

(22) Filed: Dec. 5, 2005

(51) Int. Cl.
*A24F 25/00* (2006.01)
*A01G 27/00* (2006.01)

(52) U.S. Cl. .............. 239/36; 239/55; 239/44; 239/53; 239/57; 239/145; 239/326; 222/175; 206/37; 224/222; 224/258

(58) Field of Classification Search ............... 239/36, 239/60, 63, 152, 55; 222/175; 206/0.5, 206/37, 38, 524.1; 224/222, 258; 43/1
See application file for complete search history.

(56) References Cited

U.S. PATENT DOCUMENTS

| | | | | |
|---|---|---|---|---|
| 2,401,253 A | * | 5/1946 | Lamb, Jr. .................. 119/654 |
| 4,302,899 A | * | 12/1981 | DeHart ............................. 43/1 |
| 4,682,715 A | * | 7/1987 | Reeves ....................... 222/175 |
| 4,735,010 A | * | 4/1988 | Grinarml .......................... 43/1 |
| 4,771,563 A | * | 9/1988 | Easley .............................. 43/1 |
| 4,944,940 A | * | 7/1990 | Christenson, II ............. 424/84 |
| 4,953,763 A | * | 9/1990 | Kierum et al. .............. 222/644 |
| 5,074,439 A | * | 12/1991 | Wilcox ....................... 222/175 |
| 5,327,667 A | * | 7/1994 | Fore ................................ 43/1 |
| 6,244,518 B1 | * | 6/2001 | Pogue ........................ 239/36 |
| 6,398,126 B1 | * | 6/2002 | Pitchford .................... 239/36 |
| 6,450,905 B1 | * | 9/2002 | Edlund ....................... 473/581 |
| 6,676,033 B1 | * | 1/2004 | Campesi, Sr. ................ 239/44 |
| 6,683,044 B1 | * | 1/2004 | Arienzo ......................... 512/5 |
| 6,712,286 B1 | * | 3/2004 | Baxter et al. ................ 239/36 |

* cited by examiner

*Primary Examiner*—Dinh Q. Nguyen

(57) ABSTRACT

A device for dispensing scent onto the ground from behind the ankle of a user during walking to attract animals. The device is comprised of a flat, rectangular body having first and second opposed sidewalls; a flexible cord; and a scent source. The body contains an aperture at a first end and a slit at a second opposed end. The slit provides access to a pocket enclosed by the sidewalls of the body. During use, the cord is inserted through the aperture of the body and detachably secured around the ankle area of a user. The scent source is located in the slit and pocket of the body. As the user walks, the body makes contact with the ground and the scent source, maintained in close proximity to the ground surface, dispenses animal scent attractant to the ground from behind the ankle area of the user.

9 Claims, 4 Drawing Sheets

DEVICE FOR DISPENSING ANIMAL SCENT ATTRACTANT FOR BEHIND ANKLE OF USER

BACKGROUND

This version of the invention is concerned with the field of devices to attract game animals during hunting. More specifically, this version of the invention is concerned with a device releasably attached to the ankle of a user, such as a hunter while said hunter is hunting, said device containing a quantity of liquid scent for attracting game animals and dispensing smell of said scent to attract game animals to the proximity of the hunter.

Prior Art

During the hunting of game animals, such as deer, various methods and devices are employed to find and attract said animals and to prevent the hunter from being detected by said animals during the hunting of said animal. Attraction devices include whistles, horns, and other apparatuses, which, for example, mimic the calls and bellows of a game animal during mating season. Other devices consist of life-like decoys ranging from a goose to a doe, which are strategically located to attract another similar type of animal. In some cases, scent attractants are spread upon a ground surface or other natural features so that pheromones or other sexually-attracting odors and smells will drift and spread over an area in which game animals are thought to frequent so as to draw said game animals to the area over which the scent attractants are dispensed. Various devices and methods have been used to dispense such scent attractants, including, but not limited to absorbent pads that are located upon a ground surface or attached to a natural feature, such as a tree branch, or an article of clothing, such as beneath the shoe of a hunter. Other devices, such as mechanical systems, are more elaborate in design and construction, generally consisting of a reservoir for storage of a quantity of liquid scent attractant, delivery means for transferring liquid scent attractant from the reservoir to the immediate atmosphere, and actuating means for determining the time to dispense liquid scent attractant, comprising either a timer, motion sensor, or the like.

The aforementioned devices and methods of attracting game animals perform their desired function with varying degrees of success. Absorbent pads attached to a natural feature, such as a tree branch, generally have a limited range over which the scent attractant is dispensed as such pads are stationary. The absorbent pads and other devices that are attached to a hunter are more effective in dispensing scent attractant over a wider geographical area as the scent attractant is dispensed to the area in which the hunter is stalking the game animal. However, many of these devices suffer from particular disadvantages and shortcomings. For example, devices attached to the bottom of a hunter's shoe or boot may become clogged or covered with dirt and debris, which obstruct or otherwise interfere with the ability of said devices to dispense scent attractant stored therein. Other devices are elaborate and cumbersome to use, generally interfering with the ability of the hunter to engage in the sort of physical activity necessary to stalk and hide from game animals. The mechanical devices that dispense scent attractant suffer from several disadvantages. They are generally the most expensive to purchase and maintain, and they are subject to mechanical failure in the field, thus jeopardizing their ability to attract game animals. What is needed then to overcome the aforementioned disadvantages of existing devices and methods for attracting game animals is the provision of a device that is relatively inexpensive to purchase and maintain, simple to use, and able to hold a quantity of liquid scent attractant sufficient to dispense scent attractant over a geographical area and for a duration needed to attract game animals for a successful hunting outing.

Discussion of the Prior Art

Numerous designs for devices and methods for attracting game animals through dispensation of animal scent attractant have been provided in the prior art. Even though these designs may be suitable for the specific individual purposes to which they address, they would not be suitable for the purposes of the present version of the invention as such designs are limited by the disadvantages and drawbacks recited earlier in this disclosure. These designs are exemplified by the following patents:

U.S. Pat. No. 4,302,899, Hunters And Trappers Scent Pad, issued to DeHart on 1 Dec. 1981;

U.S. Pat. No. 4,682,715, Detachable Shoe-Lure Dispenser, issued to Reeves on 28 Jul. 1987;

U.S. Pat. No. 4,735,010, Scent Dispenser For Attachment Under A Shoe, issued to Grinarmi on 5 Apr. 1988;

U.S. Pat. No. 4,771,563, Environment Enhancement Device For Animal Scent Used By Hunter, issued to Easley on 20 Sep. 1988;

U.S. Pat. No. 4,944,940, Buck Lure, issued to Christenson, II on 31 Jul. 1990;

U.S. Pat. No. 4,953,763, Animal Scent Dispensing Apparatus, issued to Kierum et al. on 4 Sep. 1990;

U.S. Pat. No. 6,450,905, Arrow Delivered Scent Dispersion Apparatus, issued to Edlund on 17 Sep. 2002; and U.S. Pat. No. 6,676,033, System For Dispensing Animal Scent Attractant, issued to Campesi, Sr. on 13 Jan. 2004;

U.S. Pat. No. 6,683,044, Animal Scent Lure And Delivery System, issued to Arienzo on 27 Jan. 2004; and U.S. Pat. No. 6,712,286, System, Apparatus, And Methods For Dispensing Scent Blocker And Animal Lure And Marking Trail During Hunting And Other Outdoor Excursions, issued to Baxter et al. on 30 Mar. 2004.

As such, it may be appreciated that there is a continuing need for a new and improved device that dispenses animal scent attractant in order to attract game animals to the vicinity of a hunter. The device for dispensing animal scent attractant that is the subject of the instant invention employs a rectangular, woven or textile body that is releasably attached to the ankle area of a hunter. When said hunter walks along the ground surface to stalk a game animal said body is dragged along said ground surface behind the hunter, dispensing scent attractant from a wick or absorbent pad releasably secured to or within said body. The device is relatively inexpensive to purchase and maintain. Furthermore, the device does not interfere with the physical motion of the hunter while said hunter is stalking or hiding from a game animal, said device delivering scent attractant in quantities sufficient to attract a game animal. In these respects, the present version of the invention substantially departs from the conventional concepts and designs of the prior art, and in so doing provides an apparatus that substantially fulfills this need. Additionally, the prior patents and commercial techniques do not suggest the present inventive combination of component elements arranged and configured as disclosed herein.

The present invention achieves its intended purposes, objects, and advantages through a new, useful and unobvious combination of method steps and component elements, with the use of a minimum number of functioning parts, at a reasonable cost to manufacture, and by employing only readily available materials.

SUMMARY

The present version of the invention, which will be described in greater detail hereinafter, relates to the field of devices to attract game animals during hunting. More specifically, this version of the invention is concerned with a device releasably attached to the ankle of a user, such as a hunter while said hunter is hunting, said device containing a quantity of liquid scent for attracting game animals and dispensing smell of said scent to attract game animals to the proximity of the hunter. My version of the invention overcomes all of the shortcomings listed previously, in addition to novel aspects that will be described in detail hereinafter.

Described briefly, according to a typical embodiment, the invention presents a device for dispensing animal scent attractant from behind the ankle of a hunter so that said attractant will attract a game animal to the geographical area being traversed by said hunter. The device is comprised of a rectangular body of woven or textile material, a cord releasably secured to the body adjacent to a first end thereof, and an absorbent wick releasably attached to the body adjacent to a second, opposed end thereof. The body is approximately twelve inches in length and two inches in width. As such, the body has first and second opposed longer side edges and first and second opposed shorter side edges. The side edges define or enclose first and second opposed sidewalls or surfaces of the body. Various camouflage patterns or patches are located on the first and second sidewalls or surfaces of the body.

A grommet with central aperture is located within the body adjacent to the first shorter side edge thereof, and a slit allowing access to a pocket within the body is located within the body adjacent to the second, opposed shorter side edge thereof. A cord is inserted through the central aperture of the grommet. Two opposed ends of the cord are disposed within a disc-shaped, spring-loaded slide. As needed, the slide can be moved to various locations upon the cord to secure the device to the ankle of a hunter when said cord is wrapped around said ankle. The wick is partially inserted though the slit into the pocket so that the wick is firmly secured to the body. The exposed end of the wick extends beyond the first longer side edge of the body for some distance.

To use the device, a quantity of liquid animal scent attractant, such as doe urine, is deposited onto the wick until the wick has reached saturation point. The cord is wrapped around the ankle of a hunter, and the spring-loaded slide is urged toward the ankle of the user, tightening the cord until said cord compresses against the ankle of the hunter. The first shorter side edge of the body is maintained in position contiguous to the ankle of the hunter above the ground surface for some distance. The second, opposed shorter side edge of the body rests upon the ground surface. As the hunter walks over the ground surface, the body is dragged upon said ground surface at the second, shorter side edge thereof. The wick dispenses animal scent attractant into the surrounding atmosphere. Depending upon the topography of the ground surface or the manner in which the hunter is walking, the body may bend, flex, coil, or otherwise contort into various shapes and configurations. As such, the wick may make contact with the ground surface or other natural features and deposit animal scent attractant thereon. Additionally, the slide can be adjusted to regulate tension on the cord to allow the body to pivot in response to the up and down motion of the user's ankle to ensure that the wick is maintained in close proximity to the ground surface, thus delivering the optimum amount of animal scent attractant to the ground. The ability of the device to dispense animal scent attractant can be further enhanced by using two or more wicks or wicks of various sizes or configurations. Over time, the animal scent attractant will attract one or more game animals to the area in which the hunter has traversed or is hiding.

My invention, therefore, resides not in any one of these features per se, but rather in the particular combination of all of them herein disclosed. It is distinguished from the prior art in this particular combination of all of its structures for the functions specified.

In order that the detailed description of the invention may be better understood and that the present contribution to the art can be more fully appreciated, additional features of the invention will be described hereinafter. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application nor is it intended to be limiting as to the scope of the invention in any way.

Accordingly, it is an object of my version of the invention to provide a low-cost, easy-to-manufacture, and easy-to-market device for dispensing animal scent attractant from behind the ankle of a user.

A further object of my version of the invention is to provide an easy-to-use and versatile device for dispensing animal scent attractant from behind the ankle of a user.

A significant object of the invention is to provide a device for dispensing animal scent attractant from behind the ankle of a user, said device comprised of a rectangular body of woven or textile material, a cord releasably secured to the body adjacent to a first end thereof, and an absorbent wick releasably attached to the body adjacent to a second, opposed end thereof, said wick able to absorb and retain therein a quantity of liquid animal scent attractant so as to dispense smell of said attractant to the atmosphere, ground surface, or other natural features.

A final but very significant object of the invention is to provide a device for dispensing animal scent attractant from behind the ankle of a user so that said attractant will attract a game animal to close proximity of the geographical area in which the user is hunting.

For a better understanding of the invention, its operating advantages and the specific objects attained by its uses, reference should be made to the accompanying drawings and descriptive matter in which there is illustrated a preferred embodiment of the invention. The foregoing has outlined some of the more pertinent objects of the invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention illustrated by the accompanying drawings.

BRIEF DESCRIPTION OF THE DRAWINGS

The foregoing and other objects, features and advantages of the invention will become more fully understood from the following description of the preferred embodiment of the invention as illustrated in the accompanying drawings in which like reference characters refer to the same parts throughout different views. The drawings are not necessarily to scale, emphasis instead being placed upon illustrating the principles of the invention.

DRAWING REFERENCE NUMERALS

10 Device For Dispensing Animal Scent Attractant From Behind Ankle Of User
12 Body
14 Side Edge
16 Side Edge
18 Side Edge
20 Side Edge
22 Sidewall
24 Sidewall
26 Stitching
28 Camouflage Pattern
30 Grommet
32 Aperture
34 Cord
36 Slide
38 Slit
40 Pocket
42 Wick
44 Pants Leg
46 Shoe
48 Ankle
50 Ground Surface

DETAILED DESCRIPTION OF THE PREFERRED EMBODIMENT

A detailed description of the preferred embodiment is provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
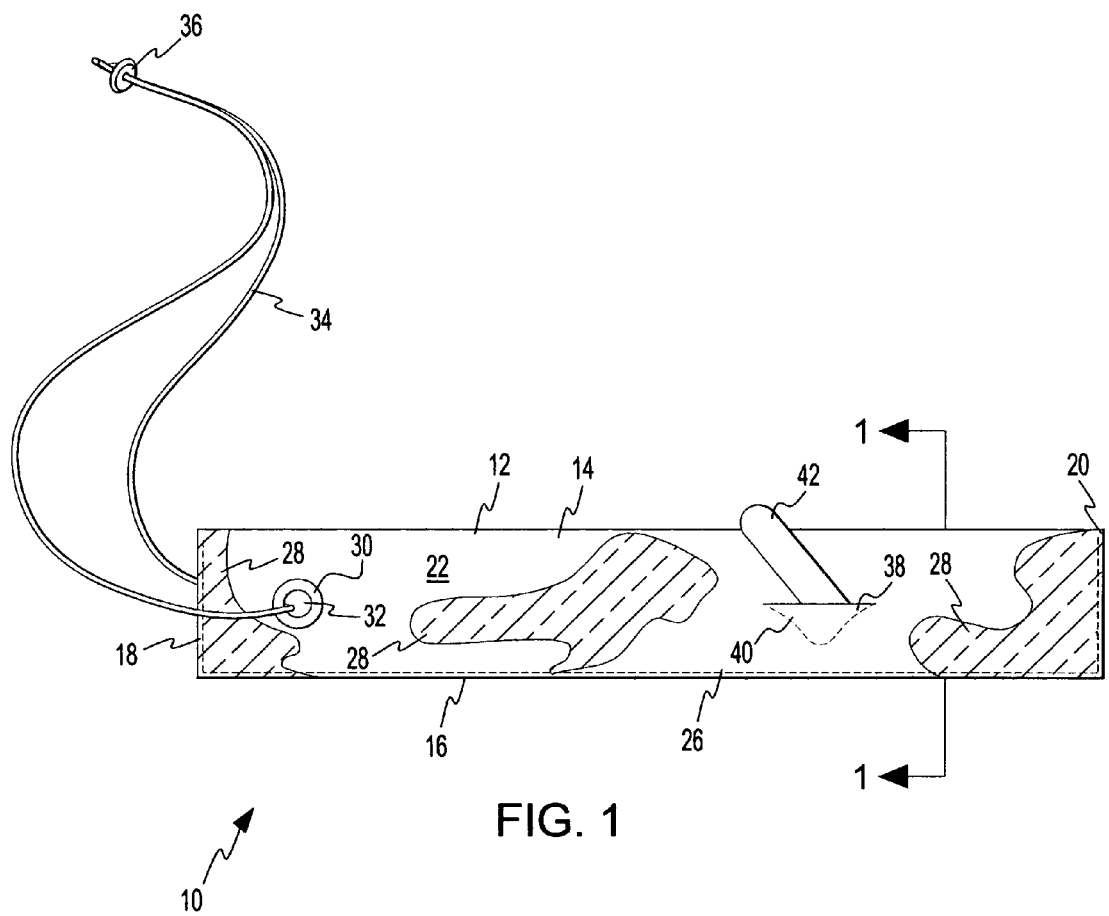
FIG. 1 is a first side elevation view of a device for dispensing animal scent attractant from behind the ankle of a user in accordance with the present version of the invention.
Figure 2:
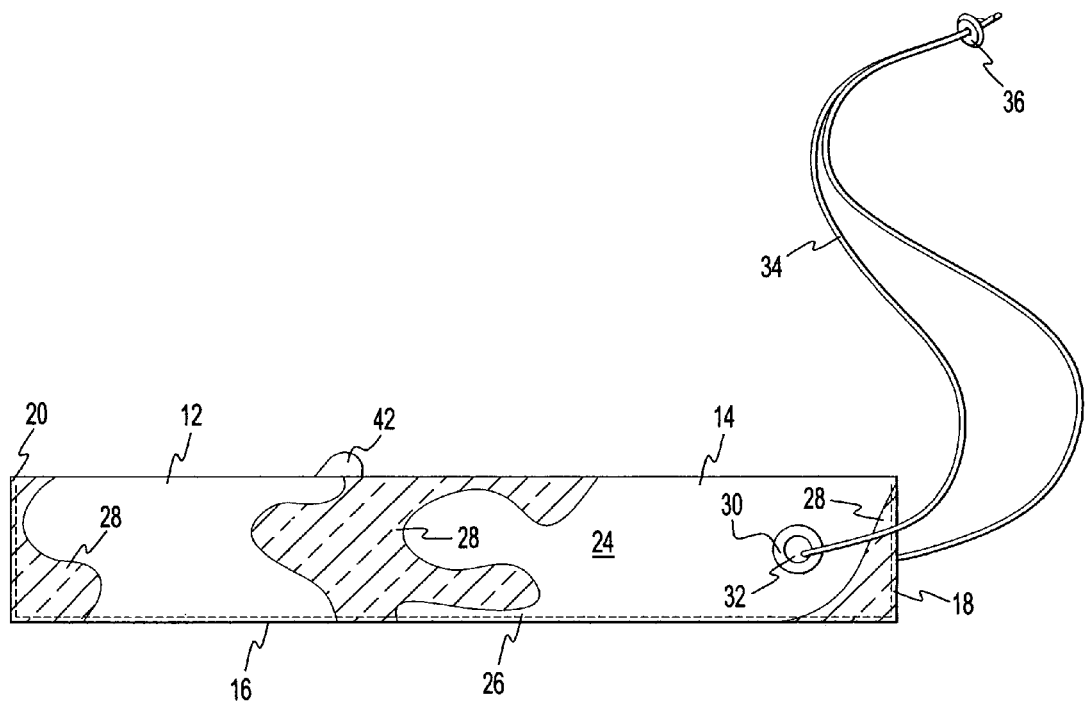
FIG. 2 is a second, opposed side elevation view of a device for dispensing animal scent attractant from behind the ankle of a user in accordance with the present version of the invention.
Figure 3:
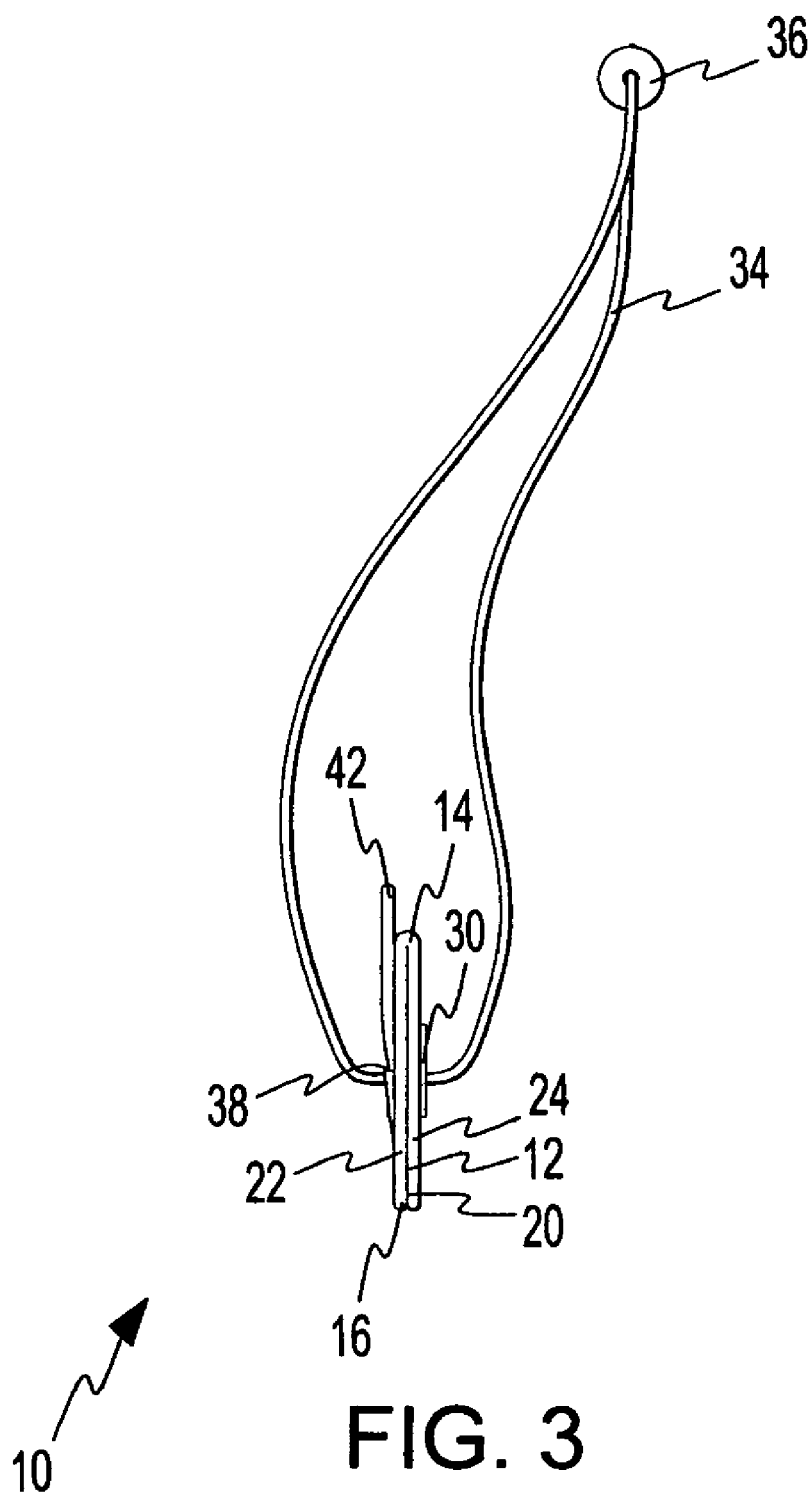
FIG. 3 is an end view of a device for dispensing animal scent attractant from behind the ankle of a user taken along line 1—1 of FIG. 1.
Figure 4:
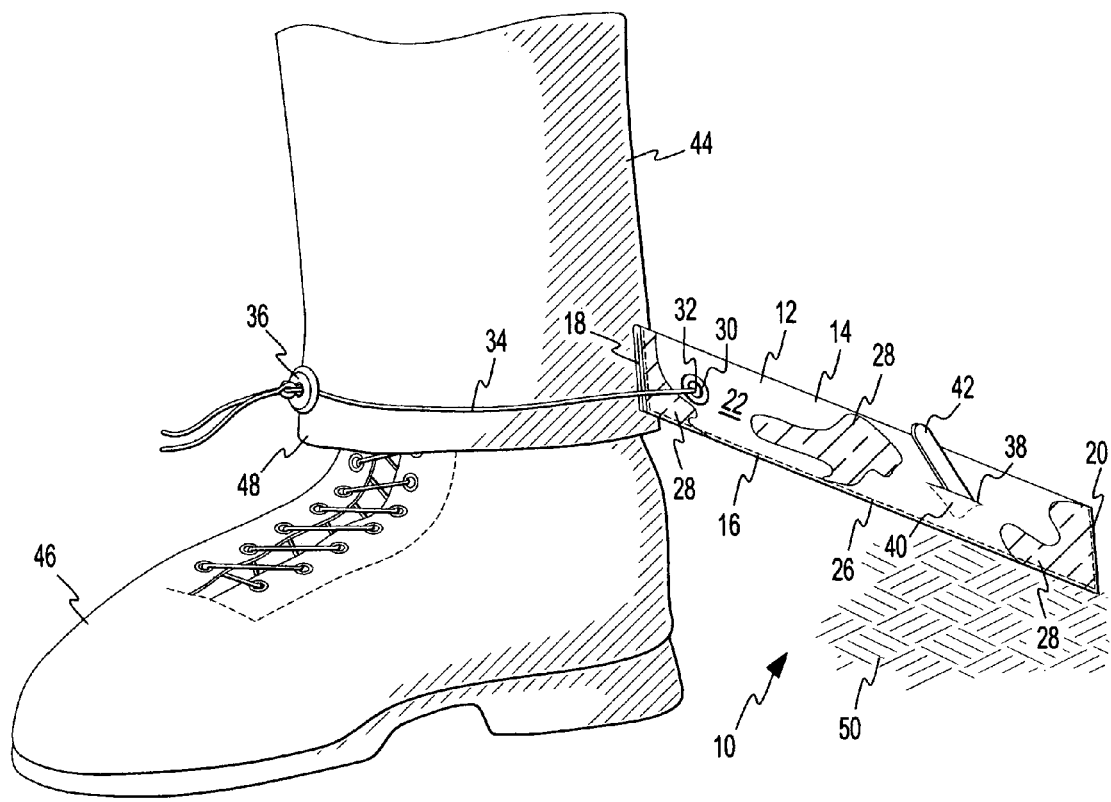
FIG. 4 is a perspective view of a device for dispensing animal scent attractant from behind the ankle of a user releasably attached to the ankle of a user in the manner for dispensing animal scent attractant to the surrounding area.

Referring now to the drawings and, in particular, to FIG. 1–FIG. 3 wherein there are illustrated a typical embodiment of the device for dispensing animal scent attractant from behind the ankle of a user 10. The present version of the invention 10 is comprised of a rectangular body 12 having first 14 and second 16 opposed longer side edges and first 18 and second 20 opposed shorter side edges. The first 14 and second 16 opposed longer side edges are generally disposed in parallel relation, and the first 18 and second 20 opposed shorter side edges are also generally disposed in parallel relation.

The body 12 is fabricated of flexible woven or textile material having dimensions of approximately 12 inches in length and approximately 4 inches in width. The body 12 is then folded in half along a longer side edge 14 thereof so that two sides are formed with said sides secured to each other to form body 12 as disclosed. More particularly, the body 12 when fabricated as such is approximately 2 inches in height between first 14 and second 16 opposed longer side edges and approximately 12 inches in length between first 18 and second 20 opposed shorter side edges. The side edges 14, 16, 18, 20 in FIG. 1 thus enclose or define a first sidewall 22 of the body 12. Conversely, the side edges 14, 16, 18, 20 as shown in FIG. 2 enclose or define a second sidewall 24 of the body 12. Referring to FIG. 1 and FIG. 2 a row of stitching 26 is located proximate to side edges 16, 18, 20, said stitching 26 functioning to secures the sidewalls 22, 24 of the body 12 to each other 22, 24. Camouflage patterns or patches 28 are located on both sidewalls 22, 24 of the body 12 in familiar random patterns or sequences so as to allow the body 12 to blend into a natural setting during use of the device 10.

A circular grommet 30 with central aperture 32 is located within the body 12 through both sidewalls 22, 24 thereof proximate to the first shorter side edge 18 of said body 12. A flexible cord 34 is inserted through the central aperture 32 of the grommet 30 in looped fashion. The cord 34 is generally comprised of first and second opposed ends with a central or middle portion located between the first and second oppose ends. In this configuration, the first and second opposed ends of the cord 34 are received within the central aperture of a spring-loaded slide 36, said slide 36 configured into a disc shape. The central or middle portion of the cord 34 occupies the central aperture 32 of the grommet 30. A slit 38 is located medially within the body 12 on one side 22 thereof proximate to the shorter side edge 20 of said body 12. The slit 38 provides access to a pocket 40, said pocket 40 defined by opposed sidewalls 22, 24 of said body 12 and said slit 38. A wick 42 is inserted through the slit 38 into the pocket 40, said wick 42 maintained securely within the pocket 40 by frictionally engaging cooperating inner surfaces of the sidewalls 22, 24 of the body 12. The wick 42 is comprised of absorbent material well known in prior art and design and has at least one rounded end as illustrated. When the wick 42 is located within the pocket 40 through the slit 38, the rounded end extends for some distance beyond the first longer side edge 14 of said body 12. The composition and size of the wick 42 allows said wick to 42 absorb and retain a quantity of liquid scent attractant sufficient to disseminate an effective quantity of scent attractant upon a ground surface, other natural features, or into the surrounding atmosphere so as to attract a game animal.

Referring to FIG. 5, therein illustrated is the device for dispensing animal scent attractant from behind ankle of user 10 releasably attached to the lower portion of the leg of a user. More particularly, the cord 34 of the device 10 is looped through the central aperture 32 of the grommet 30 of the body 12 and around the lower end of a pants leg 44 worn by said user. The lower end of the pants leg 44 partially covers a shoe or boot 46 worn by the user with said pants leg 44 and boot 46 substantially covering the ankle 48 area of said user. The cord 34 thus encloses the lower end of the pants leg 44, portion of boot 46 concealed by said lower end of the pants leg 44, and ankle 48 of user concealed by boot 46 and lower end of pants leg 44. The cord 34 is secured to the lower end of the pants leg 44 by urging the slide 36 over the cord 34 towards the pants leg 44 until the cord 34 and slide 36 compress against or frictionally engage said pants leg 44. In this configuration, the first shorter side edge 18 of the body 12 is positioned contiguous to the lower end of the pants leg 44, above the opposed second shorter side edge 20 of said body and ground surface 50 on which said side edge 20 rests. The wick 42 is saturated with animal scent attractant, such as doe urine in the hunting of a male deer or buck. In this manner, the exposed end of the wick 42, situated between the lower end of the pants leg 44 at the first shorter side edge 18 of the body 12 and ground surface 50 at the second shorter side edge 20 of the body 12, can dispense attractant scent to the ground surface 50, adjacent natural features, or the atmosphere so as to attract game animals for hunting. If the wick 42 makes contact with the ground surface 50 at the rounded end thereof, the curved surface of the rounded end allows the wick 42 to move smoothly over the ground surface 50. The capability of the wick 42 to deliver scent attractant can be enhanced by employing physically larger wicks, thereby occupying more of the pocket 40, or by using more than one wick 42.

As the user walks in a normal manner, the body 12 may drag along the ground surface 50 upon the second longer side edge 16 or the junction of the second longer side edge 16 with the shorter side edge 20 thereof. Alternately, the device 10 may react to the surface topography of said ground surface 50 or walking patterns of the user and twist, bend, coil, flex, uncoil, or otherwise conform to the terrain and features of the ground surface 50 to optimize dispensation of animal scent attractant upon the ground surface 50, adjacent natural features, or into the surrounding atmosphere. In either case, the body 12 along one of its side edges 14, 16, 18, 20, sidewalls 22, 24, or combination thereof can make contact with the ground surface 50 as the user walks, hikes, or otherwise moves over and across various ground surfaces 50. The body 12 at portions of the longer side edges 14, 16 and sidewalls 22, 24 proximate to the second shorter side edge 20 will stay in close proximity to the ground surface 50, thus ensuring that the wick 42 is maintained close to the ground surface 50 at all time.

Additionally, the body 12 is able to pivot in response to the walking motion of a user whereby the ankle 48 of a user is raised and lowered during completion of a step. With this feature, the body 12 can make continual contact with the ground surface 50 during walking, so as to ensure that the wick 42 in maintained as close as possible to the ground surface 50. The body 12 pivots by means of the grommet 30 rotating around the portion of the cord 34 occupying the aperture 32 of the grommet 30. As the ankle 48 area of a user is raised, the first shorter side edge 18 of the body 12 is raised above the second shorter side edge 20 of the body 12. Conversely, as the ankle 48 area of a user is lowered, the first shorter side edge 18 of the body 12 is lowered to be generally level with the second shorter side edge 20 of the body 12 at completion of the step. The degree of pivoting by the body 12 can be adjusted by relocating the slide 36 upon the flexible cord 34. The position of the slide 36 upon the flexible cord 34 functions to tighten or loosen the flexible cord 34 around the ankle 48 area of a user, thus varying the amount of pressure the flexible cord 34 exerts upon the body 12, which can either retard or facilitate pivoting.

While this version of the invention has been illustrated and described in detail in the drawings and foregoing description, the same is to be considered as illustrative and not restrictive in character, it being understood that only the preferred embodiment has been shown and described and that all changes and modifications that come within the spirit of the version of the invention are desired to be protected. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

CONCLUSION AND SCOPE OF INVENTION

From the foregoing, it will be understood by persons skilled in the art that an improved device for dispensing animal scent attractant from behind ankle of user has been provided. The invention is relatively simple and easy to manufacture, yet affords a variety of uses. While my description contains many specificities, these should not be construed as limitations on the scope of the version of the invention, but rather as an exemplification of the preferred embodiment thereof. The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention. Although this invention has been described in its preferred form with a certain degree of particularity, it is understood that the present disclosure of the preferred form has been made only by way of example and numerous changes in the details of construction and combination and arrangement of parts may be resorted to without departing from the spirit and scope of the invention as defined by the appended claims.

What is claimed is:

1. A device for dispensing scent onto the ground during walking to attract animals comprising:

a) a flat, rectangular body having first and second opposed shorter side edges, first and second opposed longer side edges, and first and second opposed sidewalls defined by side edges;

b) a flexible cord releasably attaching the body to an ankle area of a user, the cord having first and second opposed ends and a central portion located between the first and second opposed ends, one end of the cord inserted through the sidewalls of the body proximate to the first shorter side edge of the body and detachably secured by a fastener to the opposed end of the cord around the ankle area of the user with the central portion of the cord located within the sidewalls of the body, the central portion of the cord supporting the body against the ankle area of the user; and c) a scent source of absorbent material containing a quantity of animal scent attractant, the scent source detachably secured to the body within one sidewall thereof proximate to the second shorter side edge of the body and dispensing animal scent attractant to a ground surface while being maintained in close proximity to the ground surface as the body is pulled over the ground surface by the flexible cord and motion of the user's ankle, wherein the scent source is a flat wick that has at least one rounded end, the rounded end of the wick extending past the adjacent longer side edge of the body when the wick is inserted in the pocket.

2. The device for dispensing scent onto the ground according to claim 1, in which the sidewalls of the body enclose a pocket.

3. The device for dispensing scent onto the ground according to claim 1, in which the body contains an aperture in both sidewalls thereof proximate to the first shorter side edge of the body.

4. The device for dispensing scent onto the ground according to claim 3, in which the aperture receives the central portion of the flexible cord when the flexible cord is secured around the ankle area of the user.

5. The device for dispensing scent onto the ground according to claim 1, in which one of the sidewalls of the body contains a slit proximate to the second shorter side edge of the body and distal from the aperture in both sidewalls of the body proximate to the first shorter side edge thereof.

6. The device for dispensing scent onto the ground according to claim 5, in which the slit provides access to the pocket enclosed by the sidewalls of the body.

7. The device for dispensing scent onto the ground according to claim 1, in which the fastener is located upon the flexible cord to regulate the force exerted upon the body by the flexible cord when the body is attached by the cord to the ankle area of the user so as to allow the body at the aperture thereof to pivot upon the flexible cord in response to up and down motion of the user's ankle area during walking.

8. The device for dispensing scent onto the ground according to claim 1, in which the fastener comprises a spring-loaded slide with central aperture.

9. The device for dispensing scent onto the ground according to claim 8, in which the central aperture of the spring-loaded slide receives the first and second opposed ends of the flexible cord, detachably securing first and second ends of the cord to each other around the ankle area of a user.

* * * * *